US00PP15847P2

(12) United States Plant Patent
Toyama

(10) Patent No.: US PP15,847 P2
(45) Date of Patent: Jul. 12, 2005

(54) CHERRY TREE 'PC7146-8'

(50) Latin Name: *Prunus avium*
Varietal Denomination: PC7146-8

(75) Inventor: Thomas K. Toyama, Eugene, OR (US)

(73) Assignee: Washington State University Research Foundation, Pullman, WA (US)

( * ) Notice: Subject to any disclaimer, the term of this patent is extended or adjusted under 35 U.S.C. 154(b) by 32 days.

(21) Appl. No.: 10/402,386

(22) Filed: Mar. 27, 2003

Related U.S. Application Data

(60) Provisional application No. 60/368,660, filed on Mar. 28, 2002.

(51) Int. Cl.[7] ..... A01H 5/00
(52) U.S. Cl. ..... Plt./181
(58) Field of Search ..... Plt./181

*Primary Examiner*—Kent Bell
(74) *Attorney, Agent, or Firm*—Stratton Ballew PLLC

(57) ABSTRACT

A new cultivar of sweet cherry (*Prunus avium*) named 'PC7146-8' is disclosed. The new cultivar is notable for its large, high quality dark red fruit of superior flavor, and for its early ripening time, a few days before 'Bing.'

3 Drawing Sheets

Latin name of the genus and species of the plant claimed: *Prunus avium.*
Variety denomination: PC7146-8.

BACKGROUND OF THE INVENTION

The new cherry tree 'PC7146-8' was developed as part of a controlled breeding program at the Washington State University Irrigated Agriculture Research and Extension Center at Prosser, Wash. It was selected from among several seedlings that resulted from a cross of 'Stella' (seed parent, unpatented) and 'Beaulieu' (pollen parent, unpatented) in 1971, and was subsequently asexually propagated by budding at Prosser. Asexual propagation of 'PC7146-8' has shown that its desirable characteristics reproduce true to form and are established and transmitted through succeeding generations.

'PC7146-8' is notable for its very large, high quality dark red fruit and superior flavor. Bloom time for the new cultivar is a few days earlier than 'Bing' (unpatented); the fruit of the new cultivar ripens a few days earlier than 'Bing'. 'PC7146-8' is self fertile. All closely observed second and third generation test trees have shown no tendency toward the cherry crinkle-leaf disorder that is common in 'Bing' as well as in several other varieties of sweet cherry.

'PC7146-8' is distinguishable from its parents 'Stella' and 'Beaulieu' by its larger size, lower susceptibility to rain-induced splitting, and improved flavor.

DETAILED BOTANICAL DESCRIPTION

Figure 1:
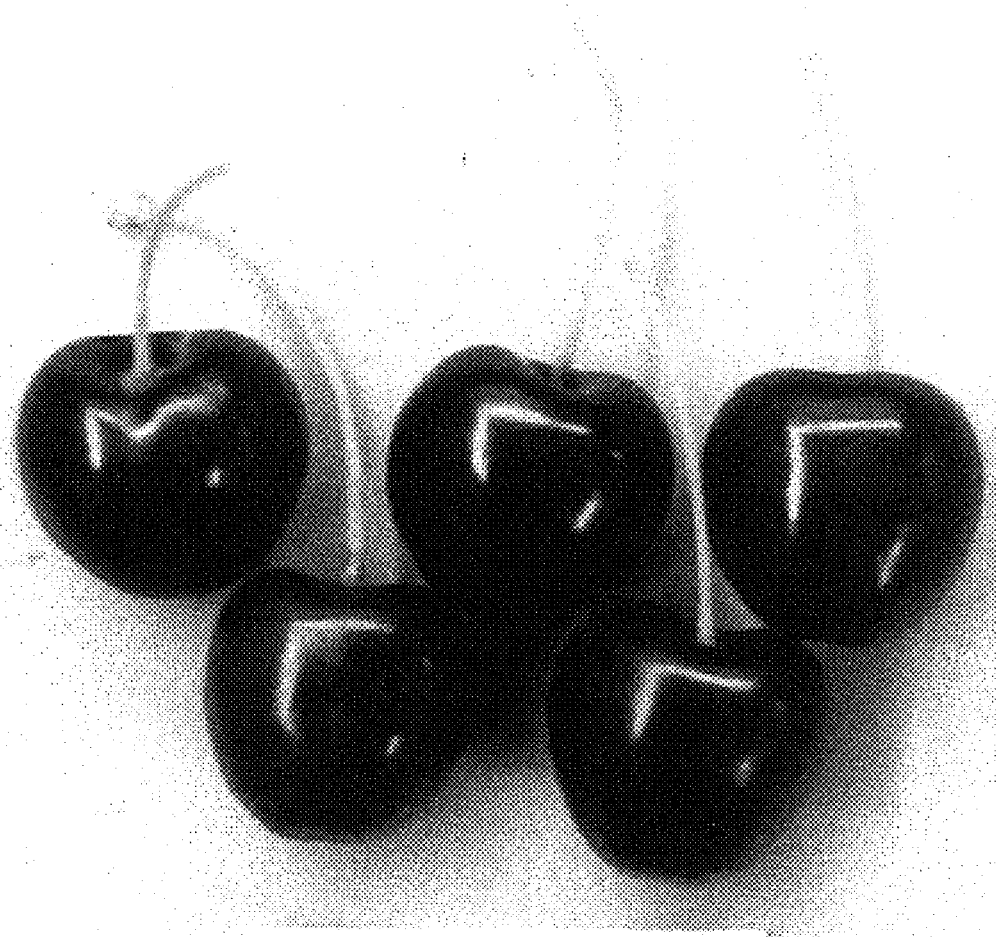
FIG. 1 is a color photograph showing the fruit of the new cultivar.
Figure 2:
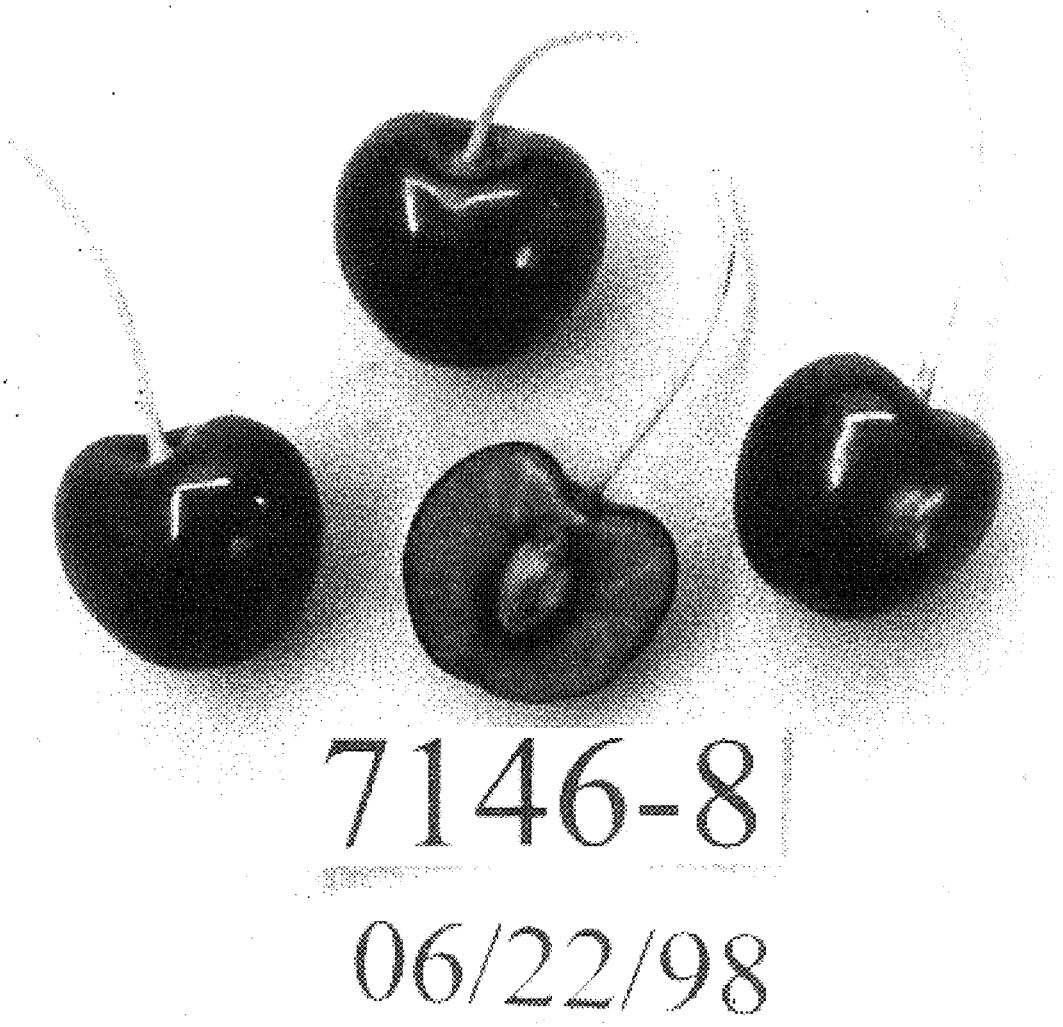
FIG. 2 is a color photograph showing whole and sectioned fruit of the new cultivar.
Figure 3:
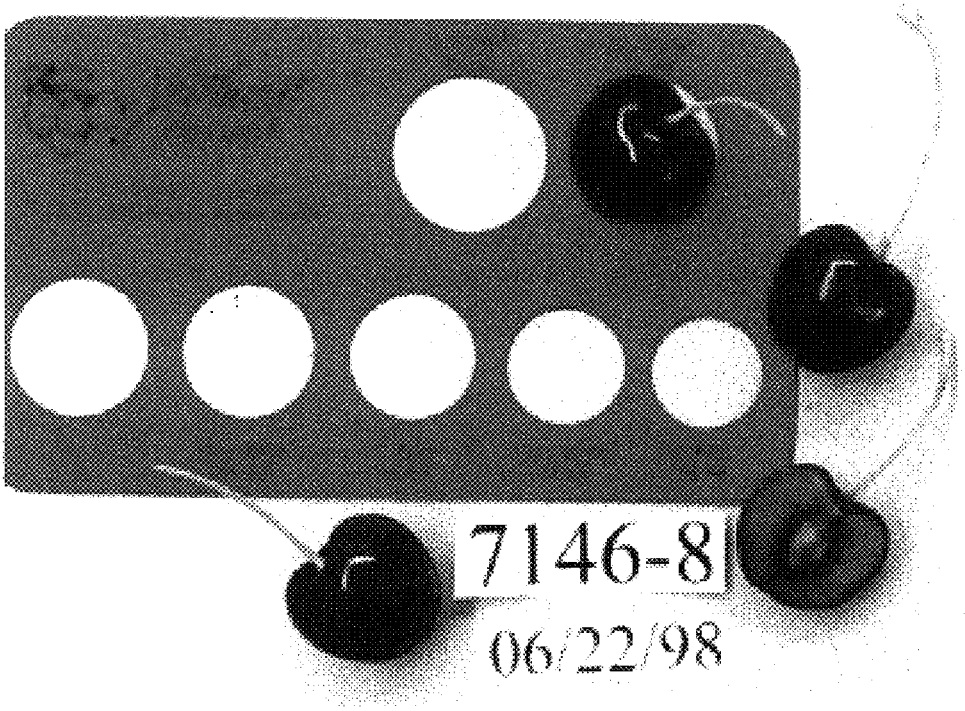
FIG. 3 is a color photograph showing whole and sectioned fruit of the new cultivar.

The following is a detailed botanical description of the new and distinct variety of *Prunus avium* named 'PC7146-8', based on observations made during the 2002 and 2004 growing seasons of 24- and 26-year old specimen trees grown near Prosser, Wash. It should be understood that the botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Size.*—Large. Average size 14 feet high, spread 18 feet wide (on 'Mazzard' rootstock) (unpatented).
- *Vigor*—Vigorous. Average growth 18 inches per year.
- *Branching habit.*—Upright-spreading.
- *Density.*—Average for sweet cherry.
- *Form.*—Round-headed when mature.
- *Hardiness.*—Hardy in area where tested; USDA hardiness zone 5b.
- *Production.*—Comparable to 'Bing'.
- *Bearing.*—Consistent, regular.

Trunk:
- *Size.*—Stocky, 64 cm diameter at 20 cm above soil level.
- *Bark texture.*—Typical for sweet cherry.
- *Bark color.*—Gray brown, 183A.
- *Lenticels.*—Numerous; Large, average 2–15 mm diameter; brown.

Branch:
- *Size.*—Stocky; Main branches average 21 cm.
- *Crotch angle of bearing branches.*—20°–90° from vertical.
- *Texture.*—Average, typical for sweet cherry.
- *Color.*—First year wood, light green143C; Second year wood, brownish gray, 183A.
- *Lenticels.*—Numerous; Medium, average 3–5 mm in diameter; brown.

Leaves: (Measurements are from mature leaves attached at midpoint of actively growing upright shoots of current season's growth.).
- *Size.*—Very large, average 13–19 cm long, 6–8 cm wide.
- *Form.*—Lanceolate with acuminate tip, cuneate to rounded base.

*Color.*—Upper surface, glossy green, 139A; Lower surface, light green, 137C.

*Margin.*—Dentate.

*Midvein.*—Large, average 1.5 mm diameter, Green, 195C.

*Petiole.*—Medium to long, average 35–45 mm long, 2–3 mm thick; Upper side red 179A; Under side green, 195C.

*Glands.*—1–2; Large, oval; Red 179A.

Flowers:

*Buds.*—4 to 7 per spur, avg. 5; Avg. 4.8 mm long; Avg. 2.6 mm wide; Greyed orange 165A;

*Pedicel.*—2–5 cm.

*Bloom time.*—First bloom Apr. 2, 2002; Full bloom Apr. 12 to 22, 2002 at Prosser, Wash.

Fruit:

*Maturity.*—Eating ripe June 18 (12 year average).

*Date of first picking.*—June 7.

*Date of last picking.*—July 28.

*Size.*—Large, average 6–11 g; diameter transversely across suture, average 2.2–2.5 cm; diameter apically average 2.2–2.5 cm.

*Form.*—Reniform, uniform, symmetrical.

*Suture.*—Very shallow.

*Cavity.*—Flattened at pedicel, rounded toward shoulders; diameter 1.1 cm shoulder to shoulder, depth 0.3 mm.

*Stem.*—Long, thin, average 3.5–5 cm in length, 0.1 mm thick; Light green 141C.

*Skin.*—Medium thickness; Medium texture; Tenacious to flesh; Susceptible to cracking caused by prolonged rains, about the same as 'Bing'; No susceptibility to cracking in dry season; Down, wanting; Color, mahogany red N186B.

*Flesh.*—Color, red, 59C; Texture, firm, crisp; Juiciness average; Eating quality, superior.

*Stone.*—Semi-free stone; Small, average 1.1 cm long, 0.8 cm wide; Oval with acuminate tip, rounded base, prominent ridge; Grey-orange 165C.

Use: Early to midseason shipping to fresh markets.

Keeping quality: Good.

Resistance to insects and diseases: Susceptible to bacterial canker (pseudomonas); no cherry crinkle-leaf noted; Susceptibility to powdery mildew is thought to be low.

Shipping quality: Firm.

It is claimed:

1. A new and distinct cherry tree, substantially as shown and described herein.

* * * * *

7146-8

06/22/98